(12) United States Patent (10) Patent No.: US 8,563,801 B2
Berland et al. (45) Date of Patent: Oct. 22, 2013

(54) SYSTEM FOR DETECTION OF UNFASTENING OR REMOVAL OF ABSORBENT ARTICLE FROM THE BODY

(75) Inventors: Carolyn Berland, Mölndal (SE); Barbro Moberg-Alehammar, Mölndal (SE)

(73) Assignee: SCA Hygiene Products AB, Göteborg (SE)

( * ) Notice: Subject to any disclaimer, the term of this patent is extended or adjusted under 35 U.S.C. 154(b) by 766 days.

(21) Appl. No.: 12/370,435

(22) Filed: Feb. 12, 2009

(65) Prior Publication Data

US 2009/0149825 A1 Jun. 11, 2009

Related U.S. Application Data

(60) Division of application No. 11/962,510, filed on Dec. 21, 2007, now Pat. No. 7,789,869, which is a continuation of application No. PCT/SE2005/001142, filed on Jul. 11, 2005.

(51) Int. Cl.
*A61F 13/15* (2006.01)

(52) U.S. Cl.
USPC .......................... 604/361; 604/389

(58) Field of Classification Search
USPC ......................... 604/361, 389–391
See application file for complete search history.

(56) References Cited

U.S. PATENT DOCUMENTS

| | | | |
|---|---|---|---|
| 2,874,695 A * | 2/1959 | Vaniman | 128/886 |
| 3,508,235 A | 4/1970 | Baisden | |
| 4,490,858 A * | 1/1985 | Batavier | 2/252 |
| 5,368,585 A | 11/1994 | Dokken | |
| 5,459,452 A * | 10/1995 | DePonte | 340/573.5 |
| 5,570,082 A * | 10/1996 | Mahgerefteh et al. | 340/604 |

(Continued)

FOREIGN PATENT DOCUMENTS

| | | |
|---|---|---|
| CN | 1380547 A | 11/2002 |
| EP | 1 038 511 A1 | 9/2000 |
| JP | 3-64605 U | 6/1991 |
| JP | 09-290001 A | 11/1997 |

(Continued)

OTHER PUBLICATIONS

English-language translation of Chinese Office Action dated Nov. 1, 2010 issued in corresponding Chinese Patent Application No. 200580051036.1.

(Continued)

*Primary Examiner* — Lynne Anderson
(74) *Attorney, Agent, or Firm* — Buchanan Ingersoll & Rooney PC

(57) ABSTRACT

A method for detecting and conveying an alarm signal, when an absorbent article is unfastened or, completely removed from the body of the wearer. The method is intended to be used in parallel with a method for detecting wetness in the absorbent article and further relates to an integrated detection-and-alarm method for detecting unfastening and/or wetness in an absorbent article. A system for detecting and conveying an alarm signal when an absorbent article is unfastened or removed from the body of the wearer and/or when the article is wet. The system includes (a) and absorbent article having at least one absorbent layer, the object to be displaced, such as a fastening system, one or more sensing devices, one or more transmitting devices, and (b) a remote receiver. Furthermore, the system relates to the use of the system in the care of children and adults suffering from incontinence and/or psychological illnesses.

25 Claims, 5 Drawing Sheets

(56) References Cited

U.S. PATENT DOCUMENTS

| | | | |
|---|---|---|---|
| 5,808,554 | A | 9/1998 | Shuminov |
| 6,097,294 | A * | 8/2000 | Hilton .................. 340/573.1 |
| 6,513,164 | B1 * | 2/2003 | Hearns .................... 2/69.5 |
| 7,295,125 | B2 * | 11/2007 | Gabriel .................. 340/604 |
| 7,658,813 | B2 | 2/2010 | Petersen |
| 2002/0076520 | A1 | 6/2002 | Neeb et al. |
| 2002/0124295 | A1 * | 9/2002 | Fenwick et al. ............ 2/69 |
| 2003/0060789 | A1 | 3/2003 | Shapira et al. |
| 2004/0036484 | A1 | 2/2004 | Tamai |
| 2004/0113801 | A1 | 6/2004 | Gustafson et al. |
| 2006/0208911 | A1 * | 9/2006 | Davis .................... 340/573.4 |

FOREIGN PATENT DOCUMENTS

| | | |
|---|---|---|
| WO | WO 97/42613 A2 | 11/1997 |
| WO | WO 00/016081 | 3/2000 |
| WO | WO 02/078513 A2 | 10/2002 |
| WO | WO 2004/021944 | 3/2004 |

OTHER PUBLICATIONS

International Search Report issued in PCT/SE2005/001142 on Feb. 3, 2006.

English-language translation of Japanese Office Action dated Jun. 21, 2011 issued in corresponding Japanese Patent Application No. 2008-521346.

* cited by examiner

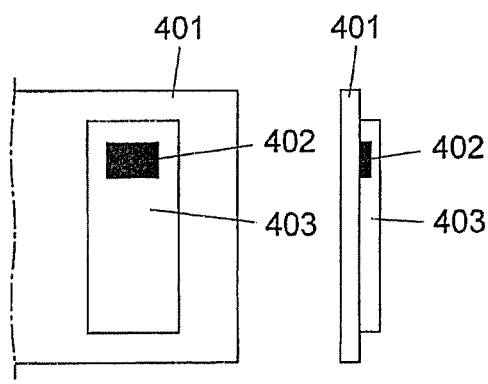
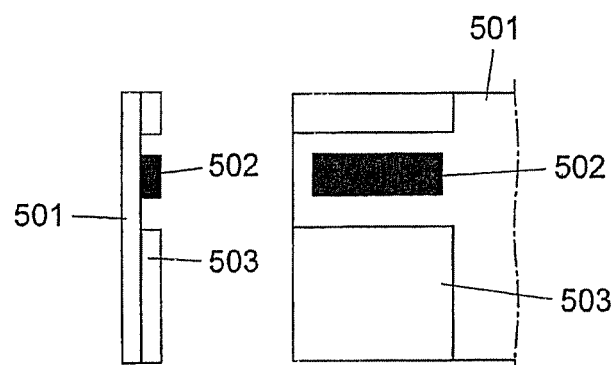

SYSTEM FOR DETECTION OF UNFASTENING OR REMOVAL OF ABSORBENT ARTICLE FROM THE BODY

CROSS REFERENCE TO RELATED APPLICATIONS

The present application is a continuation of PCT/SE2005/001142, filed Jul. 11, 2005, the entire contents of which is incorporated herein by reference.

FIELD OF THE INVENTION

This disclosure relates to a method for detecting when an absorbent article is unfastened or alternatively, completely removed from the body of the wearer, and when so, remotely indicate said unfastening. The disclosure is intended to be used in parallel with a method for detecting wetness in the absorbent article and further relates to an integrated detection-and-alarm method for detecting unfastening and/or wetness in an absorbent article. The disclosure further relates to a system for detecting when an absorbent article is unfastened or removed from the body of the wearer and/or when said article is wet, and when so, conveying an alarm signal. Furthermore, the disclosure relates to the use of said system in the care of children and adults suffering from incontinence and/or psychological illnesses, such as dementia.

BACKGROUND

Absorbent articles, such as diapers for infants and adults, sanitary napkins, and adult incontinence garments, are well known within the art and used widely. Most such products today are used on a single-use basis. The single-use basis of such disposable products have led to the development of a wide assortment of different products to meet specific requirements, e.g. in infant and toddler care, as well as in adults suffering from incontinence. The main purpose of such absorbent articles is normally to absorb, retain and isolate body waste products, such as urine, feces or blood.

Absorbent articles which respond to an event, such as urination or defecation, related to the absorption of a fluid into or onto the product, are also well known within the art. This response is normally a signal after the event has occurred and is based on a measure of, for example, wetness, temperature or mass change. The signal may be an optical signal, including visual signals, an audio signal, a chemical signal or an electrical signal. The signal can give the wearer himself/herself or nursing aid feedback information that an event has occurred, which would ease clean-up procedures for both parties.

Many of these articles incorporate sensors, the latter of which may function in a wide variety of ways. For example:

WO 2004/021944 discloses a disposable sensoring absorbent structure for detecting wetness, comprising at least one absorbent layer and at least one sensing device comprising a magnetoelastic film. The absorbent structure enables means and methods for monitoring the status, e.g. wetness, at least one biological analyte and/or at least one chemical analyte, in an absorbent article.

WO 00/16081 discloses a system comprising a resonant circuit which is at least partly formed from a moisture sensitive material, the electrical resistance of which increases when the material comes into contact with moisture. The system also comprises at least one electronic sensor for detecting the presence of moisture, and at least one reading device for obtaining information from the sensor about the presence of moisture.

U.S. Pat. No. 5,808,554 discloses a garment diaper detector for detecting wetness conditions in diapers or undergarments comprising a capacitive sensor located within a housing and affixed to the exterior surface of the garment being monitored. The sensor is comprised of two substantially solid, coplanar conductor plates affixed to a common substrate and has a very high dynamic range. When the inside of the garment becomes wet, the capacitance between the spaced conductors rises above a predetermined value whereupon the detector provides an output to a transmitter or an alarm. One particular group of direct users or wearers of such absorbent articles would include psychiatric patients suffering from dementia or other psychological illnesses, who additionally suffer from varying degrees of incontinence. These persons may not feel any inhibitions about excretory functions and may remove their incontinence garments either before urination/defecation or immediately after, thereby contaminating themselves and/or their surroundings, resulting in unpleasant clean-up activities for the nursing staff.

In such a case, the presence of an "unfastening" sensor or detector in the incontinence garment would be contemplated to be of great utility and advantage. Such a sensor would register and raise an alarm when the incontinence article is unfastened or completely removed from the body of the wearer.

The presence of a removal sensor would also be anticipated to be of utility for normal wearers such as children or persons suffering from incontinence problems, where, for example, the accidental removal of absorbent articles during sleep would lead to an alarm signal. None of the above cited art describes absorbent articles comprising a sensor for detection of unfastening or complete removal from the body of the wearer.

OBJECTS AND SUMMARY

The disclosure provides a method for detecting when an absorbent article is unfastened or alternatively, completely removed from the body of the wearer and conveying an alarm signal to the direct user or wearer, or indirect user, such as the nursing staff.

The method comprises (a) detecting the displacement of at least one object, such as a fastening device, and (b) conveying an alarm to a remote receiver.

Said method may be used in parallel with a method for detecting wetness in the absorbent article, such as the method disclosed in patent application WO 2004/021944, which is incorporated herein by reference. The method is a method for remotely detecting when an absorbent article is unfastened or removed from the body of the wearer comprising the following steps:

providing said absorbent article with a fastening system comprising at least a first and a second part, said parts being devised to be separated when the absorbent article is not attached to the wearer, and being devised to be close together when said article is attached to the wearer, where said first part is provided with an area that has the capability of influencing a resonant entity arranged at or close to said second part of said fastening system;

fastening said absorbent article to a wearer—reading a resonant frequency and/or a signal strength of a signal emitted from said resonant entity;

determining, based on said read frequency and/or signal strength, the state of the absorbent article as being unfastened/removed on the one hand or correctly fastened on the other hand. In one type of embodiments said resonant frequency assumes a first value when the absorbent article is correctly fastened to the wearer, and a second value when the absorbent article is unfastened or removed from said wearer. The method in this case further comprises the steps of determining whether a read frequency is the first frequency or the second frequency. The disclosure further relates to the use of said integrated method in the manufacture of a system for detecting and conveying an alarm signal when an absorbent article is unfastened or removed from the body of the wearer and/or when said article is wet.

The disclosure thus relates also to a system for detecting and conveying an alarm signal when an absorbent article is unfastened or removed from the body of the wearer and/or when said article is wet.

According to a preferred embodiment, the system comprises (a) an absorbent article comprising at least one absorbent layer, the object to be displaced, such as a fastening system, one or more sensing devices, one or more transmitting devices, and (b) a remote receiver.

In one embodiment, the one or more sensing device(s) detects oscillational differences arising due to an increase or a decrease in the magnetic bias-field corresponding to the displacement of said object. In such an embodiment, the preferred sensing device is a magnetoelastic film.

In another embodiment, the one or more sensing device(s) comprises a resonant circuit comprising inductive, capacitive and connective elements, and where at least one of said elements are arranged such that an electrical property of said element or elements are changed when the absorbent article is displaced or removed.

In one embodiment, the system comprises a remote receiver which is a handheld unit.

In another embodiment, the system comprises a remote receiver which is a stationary unit. In another aspect, it relates to the use of said system in the care of children and adults suffering from incontinence and/or psychological illnesses, such as dementia.

BRIEF DESCRIPTION OF THE DRAWINGS

FIGS. 4(a) and (b) show the frontal and side view illustrations of the hook fastening device (401) comprising a carrier material.

FIGS. 5(a) and (b) show the frontal and side view illustrations of another embodiment of the fastening device, where the permanent magnet is free from the hook material.

DETAILED DESCRIPTION OF THE PREFERRED EMBODIMENTS

Definitions

Figure 1:
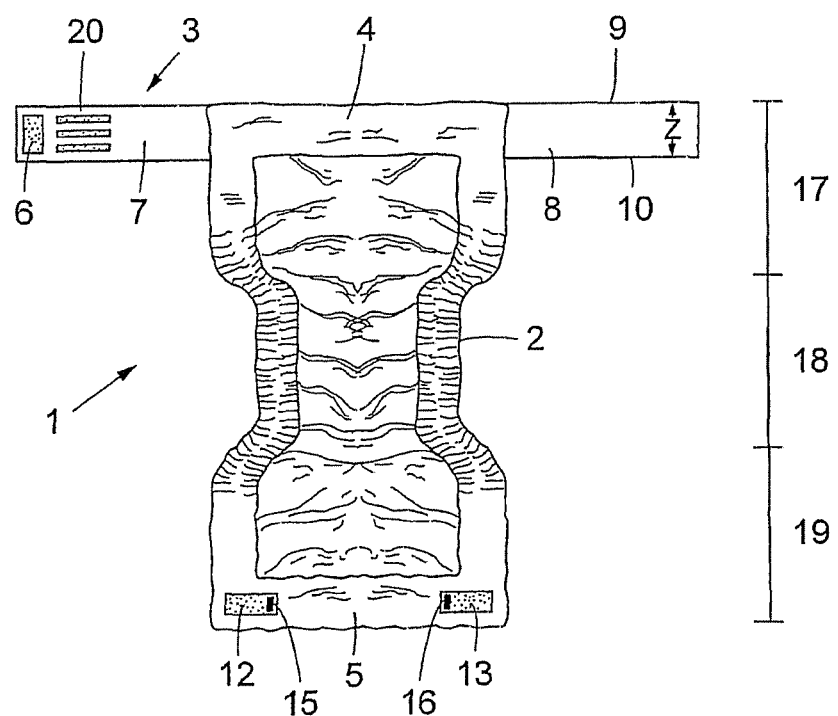
FIG. 1 shows a belt-diaper (1) having a general T-shaped configuration and comprising an absorbent structure (2) and a fastening device in the shape of a belt (3).

As used herein, the term "absorbent article" refers to a device that absorbs, retains and contains body waste or body exudates, such as urine, feces or blood.

In use, the device is placed against or otherwise positioned in close proximity to the body of the wearer.

The term "disposable" refers to an absorbent article which is not intended to be laundered, restored or reused as an absorbent article. Such an absorbent article is intended to be discarded after a single use. The single use does not however, exclude the product from being recycled, made into compost or otherwise disposed of, in an environmentally compatible manner.

The term "sensor", "sensing device" or "detector" is used interchangeably and herein intended to mean a device that is capable of detecting an event or alternatively, a parameter that is associated with an event. A parameter associated with an event is any measurable signal that correlates with the occurrence of an event within the framework of the system, i.e., a signal caused by the waste, the wearer, or a component thereof. Sensors include all embodiments responding to one or more specific inputs.

The term "sensoring" or "sensing" or "detecting" refers to means and methods capable of detecting an event or a parameter associated with an event, using, for example, a sensoring device.

The term "wetness" is herein intended to mean the condition of being wet, humid, damp or alternatively, containing or being covered by a liquid, especially water.

The term "diaper" is herein intended to mean an absorbent article generally worn about the lower portion of the torso by infants, toddlers and persons suffering from incontinence. The term "user" as used herein may refer to (a) the direct user or wearer of an absorbent article, or alternatively, (b) the indirect user or nursing personnel who have responsibility for the care of the wearer of the absorbent article.

The term "magnetostriction" refers to a common phenomena observed in magnetic materials, and is said to occur when the dimensions of a magnetic material change after being magnetized. The size or enormity of the dimensional change depends on temperature, magnetization in the material and of course, on the material properties. Magnetostriction is due to the interaction between the atomic magnetic moments in the material.

The term "magnetoacoustic resonant frequency" refers to an oscillation frequency which is manifest when a magnetic material is excited by a magnetic field and stores magnetic energy in a magnetoelastic mode. When the magnetic field is switched off, the material shows damped oscillation with a specific frequency, refered to as the magnetoacoustic resonant frequency.

The term "carrier material" as used herein refers to the material or fabric covering the hook fastening device, as depicted in FIG. 4. The carrier material may be, for example, a spunbonded nonwoven with a basis weight of about 25-60 g/m$^2$. It is preferably made of polyproplyene fibers. However, any conventional material may be used.

The term "resonant circuit" as used herein refers to an electric circuit where the impedance or the damping of said circuit is frequency dependent.

The term "resonant entity" refers to an entity, being electric, magnetic, mechanic, magnetostrictive or otherwise in nature, where the damping of said entity is frequency dependent.

Terminology and Related Subject Matter:
Absorbent Article

In normal use, an absorbent article, such as a diaper, a diaper of a reclosable pant type, an incontinence garment, a sanitary napkin, serves to absorb, retain and isolate body wastes or body exudates and discharges, for example, urine, feces, blood, menstruation blood, fluid matter from wounds and sores.

In one embodiment of the absorbent article, the absorbent layer comprised in the absorbent article, comprises at least one acquisition layer, at least one storage layer, and optionally one or more wicking layers. The acquisition layer is intended to take up fluid and to disperse said fluid to the wicking and storage layer(s).

In another embodiment, at least one of the above said acquisition, storage or wicking layer(s) comprises 0-100% superabsorbent material.

In further embodiments, said acquisition, storage or wicking layer(s) may comprise 0-95%, 20-100%, 0-30%, 20-90%, or 30-40% of superabsorbent material.

Hook and Loop Fastening

Hook and loop fastening refers to a type of VELCRO fastening, i.e., a fastening method where one of the surfaces that are to be joined comprises a plurality of small hooks. The other surface comprises a plurality of small loops.

Magnetoelastic Film

A magnetoelastic film is one type of magnetoelastic sensor. Magnetoelastic sensors have been described by Grimes et al., (Biomedical Microdevices, 2:51-60, 1999).

When a magnetic material is excited by an externally applied magnetic pulse or field, it stores magnetic energy in a magnetoelastic mode. When the field is switched off, the material shows damped oscillation with a specific frequency, the magnetoacoustic resonant frequency. These oscillations give rise to a magnetic flux that varies with time, which can be remotely detected by a pick-up coil.

The changes in resonant frequency may be monitored so as to measure or detect multiple environmental parameters. Measurements of temperature, pressure, viscosity, using this method are described in Grimes et al. (Biomedical Microdevices, 2:51-60, 1999).

It is also possible to excite the material with a continuous magnetic field showing a frequency corresponding to or close to the magnetoacoustic resonant frequency and measure the response from the material instead, such as the damped magnetic response from the material between the pulses. At the resonant frequency the response from the material is maximal.

Additionally, when a magnetic field is applied to a magnetic material, such as a ferromagnetic material, the dimension of the material changes. This effect is called magnetostriction, as defined earlier. The size of the dimensional changes of the material is governed by the magnetostriction constant. Magnetostriction can be observed in many materials, for instance, in iron, nickel, cobolt, rare earth metals as well as in different alloys such as iron-nickel alloys, ferrites, e.g. spinel type ferrites ($Fe_3O_4$, $MnFe_2O_4$), and silicon-iron alloys.

The magnetoelastic film used in the invention shows magnetorestriction and may also comprise amorphous magnetic material, alloys or mixtures thereof. Amorphous magnetic material is very easy to magnetically saturate and shows a small magnetic anisotropy. In alloyed amorphous magnetic material, magnetostriction is also present, and the amount of magnetostriction depends on the exact composition of the alloy. Examples of amorphous alloys are metglases such as $Fe_{40}Ni_{38}Mo_4B_{18}$, e.g. Metglas 282MB™ (Honeywell Amorphous Metals, Pittsburg, Pa., USA), $(FeCo)_{80}B_{20}$, $(CoNi)_{80}B_{20}$, $(FeNi)_{80}B_{20}$.

One embodiment uses METGLAS® material from Honeywell (Honeywell Amorphous Metals, Pittsburg, Pa., USA) as the magnetoelastic material, such as METGLAS® 2826MB.

Suitable magnetoelastic films may be any film possessing a non-zero magnetostriction and a high magnetoelastic coupling, such as an iron-nickel alloy, rare earth metals, ferrites, and the different alloys and mixtures disclosed above. A suitable film thickness of said magnetoelastic films is about 0.01-1000 µm, such as from about 0.01 to about 200 µm, such as from about 5 to about 100 µm, such as from about 0.01 to about 100 µm. The thickness of the film may be much less than the width and the length of the film.

One way of further enhancing the magnetostrictive effect is to include a magnetic bias field. A magnetic bias field has an optimal magnetic bias field, giving an optimal magnetoacoustic effect, and further giving an optimal signal from the magnetoacoustic effect (Grimes et al., Sensors and Actuators, B71:112-117, 2000). In one embodiment, the magnetic bias field is generated by a permanent magnet, placed in connection with the magnetoelastic film. The permanent magnet may be in the form of small metallic pieces of various shapes and sizes (such as those used domestically as kitchen pin-up devices on the refrigerator), powder, granules, film, magnetic ink, and other forms.

The disclosed embodiments provide a convenient and inexpensive method for detecting and conveying an alarm signal to the direct user (such as the wearer), or indirect user (such as the nursing staff), when an absorbent article is unfastened or alternatively, completely removed from the body of the wearer.

The alarm signal thus represents feedback information that an event has occurred.

The embodiments would also permit convenient monitoring, through remote access, of the status of the wearer (i.e., absorbent article on or off), as well as continuous monitoring of the status over time by the nursing staff.

The method comprises (a) detecting the displacement of at least one object, such as a fastening device, and (b) conveying an alarm to a remote receiver. The remote receiver may be in the form of a handheld unit or a stationary unit permanently placed at a suitable location.

Said method is intended to be used in parallel with a method for detecting wetness in the absorbent article, such as the method disclosed in patent application WO 2004/021944, described briefly in the background section and which is incorporated here by reference. Said method disclosed the use of a sensing device comprising a magnetoelastic film with a thickness of between about 0.01-1000 µm for detecting the presence of moisture and/or biological analytes and chemical analytes. The present disclosure thus further relates to an integrated detection-and-alarm method for detecting unfastening and/or wetness of/in an absorbent article.

The disclosure further relates to the use of said integrated method in the manufacture of a system for detecting and conveying an alarm signal when an absorbent article is unfastened or removed from the body of the wearer and optionally when said article is wet.

The disclosure thus relates also to a system for detecting and conveying an alarm signal when an absorbent article is unfastened or removed from the body of the wearer and optionally when said article is wet.

According to a preferred embodiment, the system comprises (a) an absorbent article comprising at least one absorbent layer, the object to be displaced, such as a fastening system, one or more sensing devices, one or more transmitting devices, and (b) a remote receiver, which houses a pickup coil. In one embodiment, the one or more sensing device(s) detects oscillational differences arising due to an increase or a decrease in the bias-field corresponding to the displacement of said object. Said sensing device may be small, optionally removable and reusable, involve a wireless, battery-less circuit, is coupled with an alarm transmitter and remote receiver. The sensing device may be packaged or encapsulated as protection against damage from, for example, mechanical pressure, which may affect the resonant frequency. Suitable encapsulation forms include encapsulation in the form of tags such as the commercially available tags from, e.g., Sensomatic (Wien, Austria), or a similar product. The encapsulation is designed or chosen in each case by the skilled man to fit a specific embodiment.

In a preferred embodiment, a magnetoelastic film is employed as the sensing device. One or more sensors may be used. Furthermore, a thin ribbon of a magnetoelastic material may be used. The magnetoacoustic resonant frequency for, for example, a thin ribbon of a magnetoelastic material is inversely proportional to the length of the ribbon. Thus, it is possible to achieve different resonant frequencies in one sensoring device. A typical magnetoelastic material which could be used in the invention is METGLAS material from Honeywell (Morristown, N.J.) In one embodiment, a magnetic bias field is generated, and a resonant entity is provided, through the presence of, for example, one or more permanent magnets which are connected to, or placed in a defined position, with respect to the one or more sensors. The permanent magnets are attached to one or more fastening devices of said absorbent article by any method commonly used in the art, or may be employed as a part of the fastening device. The permanent magnets may be in the form of small metallic pieces of various shapes and sizes, powder, granules, film, magnetic ink, or other forms.

When the fastening device(s) are moved away from the sensor(s), as in the situation when the absorbent article is unfastened, the magnetic field will change and the sensor(s) detect oscillational differences arising due to an increase or a decrease in the bias-field corresponding to the displacement of said fastening device(s). As an example, in a diaper-type garment, the sensor response might involve a resonant entity which detects whether the fastening device such as a tape or a belt is in contact with the front panel of the diaper.

This effect is supported by studies in the literature (Ohizumi, S., "Physics of Ferromagnetism", Oxford, Oxford University Press, 1997; O'Handley, R. C., "Modern Magnetic Materials, Principles and Applications", New York, John Wiley & Sons Inc., 2000). A comparison of the magnetoacoustic effect appearing when a magnetic bias field is first applied, or alternatively, as in this example, obtained from a permanent magnet (a) in the neighborhood of a magnetoelastic (such as METGLAS®) film), and then (b) over said film, shows that the signal from the magnetoacoustic oscillations increases significantly, and that it is even possible to see higher harmonics of the magneto-acoustic oscillations. This is due to the fact that the magnetoelastic effect is enhanced when the magnetic field is increased over the sample.

The amplitude of the applied magnetic field should be large enough to magnetize the material, such as the magnetoelastic film, to a certain amount in order to achieve a sufficiently large change in material dimensions. The specific magnetic fields may therefore be optimized for each magnetostrictive material chosen.

A magnetic field amplitude of, for example, 0.06 mT at the film, has been assessed by the inventors to be high enough in order to detect magnetoacoustic signals. Magnetic pulses of 1 kHz with a duty cycle of 20% are typically used, but other frequencies and duty cycles may also be used. A magnetic field in the range of 0.05 mT to 0.1 mT will create sufficient magnetization in the magnetoelastic film. The exact value depends on the chosen material in the magnetoelastic film, and may thus be optimized for each embodiment. The exact values of the pulse frequency, duty cycle and field amplitude at the film could, in a similar way, be optimized when the material of the magnetoelastic film and the application of the sensor system are chosen. Also, the distance of the remote receiver of the alarm signal (such as a handheld or stationary unit) should be considered here and the value of the maximum distance between the remote receiver and the magnetoelastic film should be defined when optimizing other parameters in the different embodiments. The minimum distance is at the outer surface of the absorbent article. The detection may be designed to enable the largest covering range about x m, where x is chosen by, for example, the nursing personnel, by proper design of an excitation coil and a pick-up coil.

In one embodiment, the detection may be designed to enable the largest covering range about x m, where x is about 0-10 m, such as about 0, 1, 2, 3, 4, 5, 6, 7, 8, 9, or 10 m.

In a further embodiment, the detection may be designed to enable the largest covering range about x m, where x is about 0-5 m.

In still a further embodiment, the detection may be designed to enable the largest covering range about x m, where x is about 0-1 m, such as about 0, 0.1, 0.2, 0.3, 0.4, 0.5, 0.6, 0.7, 0.8, 0.9, or 1 m.

Detection of the magnetoacoustic resonant frequency is effected through the pick-up coil housed within the remote receiver, which detects the response from the material.

In one embodiment, the system comprises a remote receiver which is a handheld unit. A typical remote receiver in the form of a hand held unit has already been described in WO 2004/021944 A1, which is incorporated by reference. The signal generator is connected to the detection circuit so that the detection circuit "knows" when a signal is sent to the excitation coil. Furthermore, the remote receiver, such as in the form of a hand held unit, may be designed to minimize the magnetic coupling between the magnetic bias field, such as from a permanent magnet, and the pick-up coil. The position of the pick-up coil with respect to the magnetic bias field may be optimized for maximum signal from the film and minimal signal due to the magnetic field from the bias field.

In another embodiment, the system comprises a remote receiver which is a stationary unit located at suitable position with reference to both the wearer and nursing staff (for example, in the wearer's or patient's bedroom) or only with reference to the nursing staff (for example, in the office of the nursing staff).

In yet another embodiment, the one or more sensing device(s) comprises a resonant electric circuit instead of a magnetoelastic film. Said embodiment comprises a first and a second electrode of a LC-circuit or LRC-circuit. Said first and second electrode is arranged as part of, or close to the fastening device of said absorbent article. The fastening device is further provided with a conductive area, e.g. a metal film, such that when the fastening device of the absorbent article is correctly closed, the conductive area makes contact to both the first and the second electrode, thereby short-circuiting said LC-circuit. When said LC-circuit is excited by an interrogation signal the response signal will be zero or close to zero, and a frequency of said signal would be different from a frequency of a signal detectable when the fastening device of said absorbent article is open or incorrectly closed. Said interrogation signal is a signal for exciting the LC-circuit. The excited LC-circuit, subsequently to the excitation, emits a radio frequency response signal. This response signal is read by the reading device, which can be part of a remote receiver.

In a further embodiment, said system comprises an absorbent article provided with a resonant electric circuit such as a LC or LRC-circuit. Said resonant electric circuit is of a sufficiently small size such that it can be arranged as part of or close to the fastening device of said absorbent article. The fastening device is further provided with a shielding means, e.g. a metal foil or metal film, such that when the fastening device of the absorbent article is correctly closed, the shielding area comes in such a position that it covers completely or such a big part of the resonant electrical circuit that said shielding means disperses an incoming radio-frequent signal, such that the underlying resonant electrical circuit does not resonate, or resonates very little.

The resonant electrical circuit is preferably arranged in the so called "Tape Landing Zone", i.e. the area of the fastening device of the absorbent article where the adhesive fastening tab is fastened. In a hook-and-loop system the corresponding zone would be the "loop zone".

According to another aspect, the disclosure relates to the use of said system in the care of children and adults suffering from incontinence and/or psychological illnesses, such as dementia.

EXAMPLES

Examples (and accompanying figures) 1-5 given below illustrate embodiments of the invention, and describe several possible embodiments of said absorbent article which is comprised in the system. These examples are present to exemplify the invention but not intended to limit in any way the invention as described herein.

Figure 2:
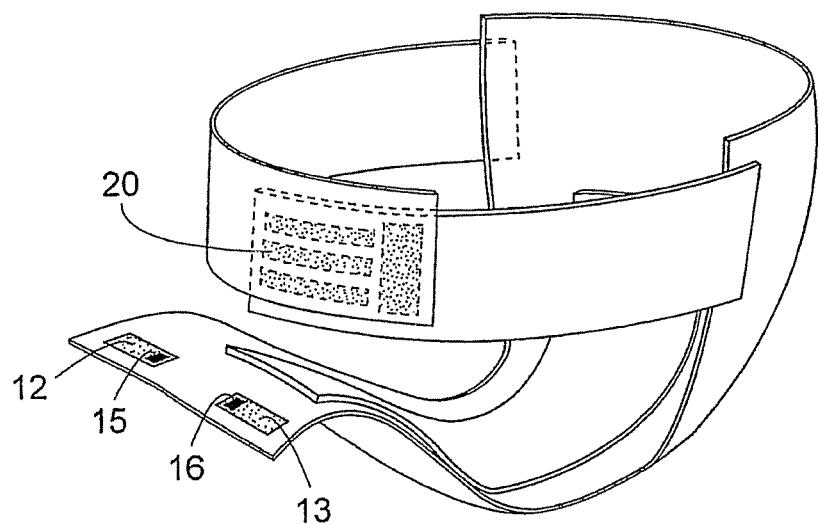
FIG. 2 shows the diaper (1) just before fastening of the front part (19) of the diaper (1) to the belt (3).

FIGS. 1 and 2 (taken together), and FIG. 3 shows two different embodiments of the invention.

Example 1

In FIG. 1, the belt-diaper (1) has a general T-shaped configuration and comprise an absorbent structure (2) placed in between a liquid permeable topsheet (4) and a liquid impermeable backsheet (5). The belt-diaper further comprises a fastening device in the shape of a belt (3). The belt consists of a first and a second belt part (7, 8) in the shown embodiment.

The belt-diaper further comprises fastening system in the shape of a belt fastening hook (6) which attaches directly onto the second belt part (8). The fastening system further includes diaper fastening hooks (12, 13). The belt comprises a nonwoven laminate with a layer of spunbonded nonwoven placed in-between and thermally bonded to two layers of carded nonwoven. In this embodiment, the nonwoven layers consist of polypropylene fibers. Each layer has a surface weight of about 22 g/m².

The diaper fastening hooks (12, 13) are placed on the liquid permeable topsheet (4) of the diaper (1) and attach directly onto the outward facing part of belt (3), as illustrated in FIG. 2. Each diaper fastening hook comprises a permanent magnet (15, 16) placed between the liquid permeable topsheet (4) and the outer surface of the diaper fastening hook (15, 16). Further details of this arrangement are shown in FIGS. 4-5. The permanent magnet may be in the form of small metallic pieces of various shapes and sizes, powder, granules, film, magnetic ink, or other forms.

A plurality of magneto-elastic films, for example, three films, are positioned inside the first belt part (7) between the carded nonwoven layer facing away from the user during use and the middle spunbonded nonwoven layer in the belt laminate. This is illustrated by three rectangular magnetoelastic films (20) shown in FIGS. 1 and 2. In further embodiments said plurality of magneto-elastic films may be placed in a lengthwise or crosswise direction of the fastening system. Placing them in a lengthwise direction allows users of different sizes to use the absorbent article without severely affecting the functionality of the invention.

In all embodiments, the films are preferably encapsulated in order to protect them from mechanical pressure.

In a further embodiment, several more sensors (20), which may possess different resonance frequencies, are placed in the absorbing article. The placement may be in the rear, in the front and on the sides of the diaper.

The placement of the sensors 20 in FIG. 1 are only to be considered as examples.

The belt diaper further comprises a front part (19) intended to be worn against the wearer's abdomen during use. A rear part (17), intended to be worn against the wearer's back during use and a crotch part (18), placed between the front part (19) and the rear part (17), intended to be worn against the wearer's genitals during use. The belt (3) is attached to the rear part (17) of the diaper (1).

FIG. 2 shows the diaper (1) just before fastening of the front part (19) of the diaper (1) to the belt (3). FIG. 1 should also be referred to for references to other parts of the diaper. The first belt part (7) is attached to the second belt part (8) via belt fastening hook (6). By doing this, the plurality of magneto elastic films (20) are exposed and positioned in close relationship to the diaper fastening hooks (12, 13) and the permanent magnets (15, 16). The absorbent core, liquid impermeable backsheet and the liquid permeable topsheet shown in the belt-diaper in FIG. 1 may have, where appropriate, the same configuration as the open diaper described in FIG. 3.

A remote unit in the form of a hand held unit or in the form of a stationary unit may then be used to establish a first frequency A which corresponds to a closed diaper. This frequency A can at any later stage be used to correlate a new measurement of a second frequency B. If the first frequency A is lower than the second frequency B then the permanent magnets (15, 16) are displaced in relationship to the plurality of magneto elastic films 20. This displacement can be correlated to the event that the fastening system of the diaper is disabled or that the function of the fastening system is reduced. When the diaper fastening system is disabled, the diaper is not in conformity with the wearer's body and the risk of leakage is thus much higher than before. The alarm signal resulting would cause a nursing aid to look into the wearer's actual situation. In one embodiment, the frequency A is stored in the hand held unit. In another embodiment, the frequency A is sent directly or indirectly to a computer which compares the frequency A with a later measured frequency B.

Both the frequencies A and B may also be compared to predetermined values corresponding to open or closed/disabled diaper.

Example 2

Figure 3A:
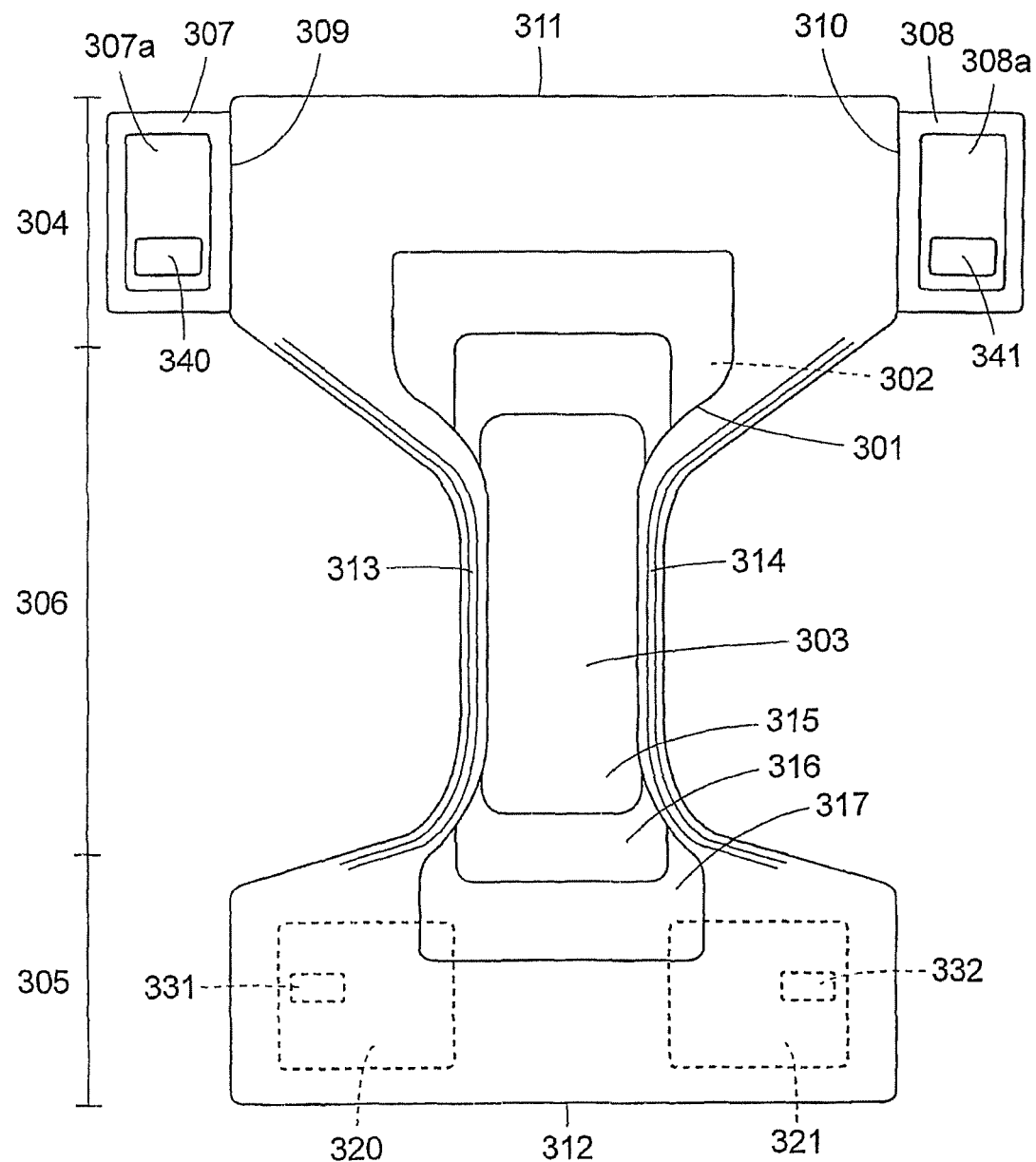
FIGS. 3a and 3b show an "open diaper" embodiment of the belt-diaper (1), in an unmounted state, FIG. 3a and in a mounted state, FIG. 3b.
Figure 3B:
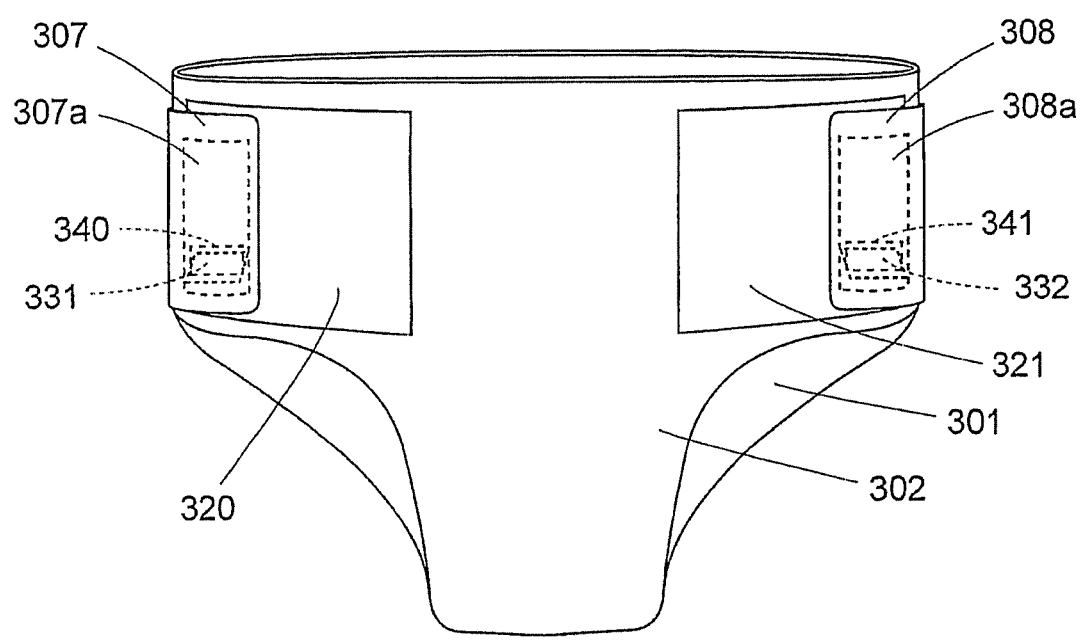

FIG. 3*a* and FIG. 3*b* show a further embodiment of the invention. FIG. 3*a* displays a diaper with tape tabs (307, 308) and two loop fastening zones (320, 321) placed on the liquid impermeable backsheet (302). The tape tabs 307, 308 are further provided with hook areas 307*a*, 307*b*. The hook areas are further each provided with a permanent magnet 340, 341. This arrangement is futher described in connection with FIG. 4.

The loop fastening zones (320, 321) comprises a conventional loop material and will therefore not be described further. Two magnetoelastic films 331, 332 are positioned between the loop fastening zones 320, 321 and the liquid impermeable backsheet. When the diaper is worn, the fastening system in the shape of the tape tabs (307, 308) with hook areas 307a, 308a and permanent magnet areas 340, 341 and the loop fastening zone (320, 321) will be close in relation to the magnetoelastic films. The frequency can then be established as described in Example 1. When the diaper is unfastened, the displacement results in an alarm signal to the wearer or nursing aid as before.

The wetting point is an area of the diaper surface onto where the body liquid or body waste first comes into contact. Obviously, it is not possible in practice to establish any specific point or area in this regard, although it can be generally accepted that the body liquid or waste will be delivered to the diaper within a given, limited area thereof. In general, this area is displaced slightly towards the front of the diaper part, in the case of both male and female wearers. Since the dispersion of the liquid in the first absorbent layer, i.e. the acquisition layer, is only slight, it is sufficient for this layer to cover solely the area of the diaper where wetting is most likely to occur. Accordingly, such aspects may be analyzed and considered when placing sensoring devices in an absorbent article, such as the diaper comprising the system.

The diaper illustrated in FIG. 3 is comprised of a liquid-permeable top sheet 301, for instance, a non-woven or perforated plastic film, a liquid impermeable back sheet 302, for instance, a plastic film or a hydrophobic non-woven material, and an absorbent structure 303 enclosed between the two layers 301, 302.

The diaper is intended to embrace the lower part of the wearer's trunk, in the manner of a pair of absorbent underpants. The diaper is provided with a back part 304 which, when the diaper is worn, will be located rearwardly on the wearer, a front part 305, which when the diaper is worn will be located forwardly on the wearer, and a narrower crotch part 306 which extends between the back part 304 and the front part 305 of the diaper and which, when the diaper is worn, is located in the crotch region of the wearer, between the thighs thereof. Fastener tabs 307, 308, with hook material, 307a, 308a, are provided on the side edges 309, 310 of the back part 304 extending in the longitudinal direction of the diaper, close to the rear waist edge 311 of said diaper, so as to enable the diaper to be secured in the desired pants-like form. When the diaper is to be used, the fastened tabs 307, 308 are fastened to the outer surface of the front diaper part 305, close to the forward waist edge 312, thereby holding the diaper together around the wearer's waist.

The diaper illustrated in FIG. 3 also includes prestretched elastic devices 313, 314 which extend along the longitudinal side edges of the diaper in the crotch part 306. The elastic devices 313, 314 may consist of any suitable material, such as elastic foam, elastic bands or covered elastic threads. For the sake of convenience, the elastic devices 313, 314 have been shown in a stretched state.

The absorbent structure 303 is comprised of mutually different layers. Nearest to the liquid permeable top sheet 301 is a thin cellulose fluff-pulp layer 315 of high critical bulk, large pore volume and low liquid-dispersion ability. By critical bulk is meant the bulk at which a cellulose body will neither collapse nor expand when becoming wet. A cellulose fluff-pulp of high critical bulk will retain an open structure of large pore volume even when wet.

Seen in a direction towards the liquid-impermeable back sheet 302, there then follows a first absorbent layer 316, which is comprised of cellulose fluff-pulp of large pore volume, high wet resilience and low liquid-dispersion ability, and a second absorbent layer 317 comprised of cellulose fluff-pulp of low pore volume, low wet resiliency and high liquid-dispersion ability. Both absorbent layers also include superabsorbent material.

The first absorbent layer 316, has an oval shape and is located generally in the crotch part 306 of the diaper, around the so-called wetting point. In other embodiments said layer 316 has a rectangular shape or other suitable shape.

The first receiving layer, i.e. the acquisition layer, in the diaper thus functions as a receiving area for discharged body liquid or waste.

CTMP fluff, CF fluff, wadding or foam is suitable for use in the first absorbent layer. SAP may be added in different proportions to this layer as well. The first absorbent layer 316 may also contain between 2-30%, such as 2-15% superabsorbent material calculated on the total dry weight of the layer in that area in which the superabsorbent material is mixed. The superabsorbent may be distributed generally uniformly in the layer, within at least one area or region thereof, and is intended to bind any liquid that remains in the layer, even when the layer has been drained by the second absorbent layer 317, which may be a wicking layer.

As mentioned previously, the superabsorbent material in the first absorbent layer should preferably have a high gel-strength, to retain an open fibre structure even when becoming wet.

The second absorbent layer 317 also contains superabsorbent material, which may be in the form of one or more layers of flakes, fibres, granules, powder or the like. The layer extends either over the whole of the absorbent layer 317 or is restricted to at least one area thereof. This area may, for instance, be slightly larger than the absorbent layer 316 and, similar to said layer, may be limited essentially to the crotch part of the diaper.

The proportion of superabsorbent included in the second absorbent layer 317 will preferably be between 2 and 60%, preferably between 19 and 50%, calculated as a fraction of the total dry weight of the layer. The super absorbent in the second absorbent layer 317 will preferably have a high gel-strength, i.e., has the ability to swell substantially unaffected by normally occurring pressure forces, so as not to block or impede dispersion of the liquid. Characteristic of these super absorbents is that they have a high degree of cross-linking which renders them more difficult to compress in comparison with a gel that has a lower degree of cross linking.

The fluff pulp in layer 317 of the second absorbent layer may comprise substantially fluff-pulp or some other absorbent material having a high liquid-dispersion capability. Chemically produced fluff-pulps, of cellulose material, generally fulfill this. The final fibres may have a weight of 140-190 µg/m, a low degree of stiffness and low wet-stability, and a critical bulk beneath 8 $cm^3$/g at 2.5 kPa.

The second layer 317 may also comprise a chosen fluff pulp, such as CTMP-pulp or chemical pulp.

Thus, discharged body fluid or waste is first collected in the first absorbent layer 316, which function as a buffer, or reservoir, this layer being successively drained as the second absorbent layer 317, absorbs and disperses the liquid waste.

It will be understood that the illustrated and described diaper is merely intended to exemplify the invention and shall not be considered to limit the scope of the invention. For instance, the shape of the diaper and its construction in other respects may be varied. Similarly, the first absorbent layer 316 may fully cover the second absorbent layer. Furthermore, the thin cellulose fluff-pulp layer 315 located nearest to the liquid-permeable top sheet layer 301, may be omitted.

It should also be noted that a diaper, as used herein, is particularly used in conjunction with incontinence, but that the invention is not limited to this particular use or any particular size or type of diaper implied thereby, but may be any diaper obvious to the person skilled in the art.

Example 3

FIG. 4a displays a hook fastening device (401) comprising a carrier material, for example, a spunbonded nonwoven with a basis weight of about 25-60 g/m². The carrier material is preferably made of polyproplyene fibers but any conventional material can be used. The carrier material further comprises a permanent magnet (402). The permanent magnet (402) is held in place by the hook material (403) which is adhered onto the carrier material with conventional hot-melt adhesive. Optionally the magnet may be adhered to the carrier material directly. The hook material (403) holds the magnet in place so that the position of the magnet is always correlated with the position of the hook material.

FIG. 4b shows a cross-sectional view along the line I-I for one embodiment of the hook fastening device.

FIG. 5a discloses another embodiment of a fastening device. In this embodiment the permanent magnet is free from said hook material. This exposes the magnetoelastic film to a stronger bias-field, which might be favorable, when the article is worn.

It should be noted that the hook material may be replaced by an adhesive film or any other known fastening material known in the art. If the fastening system consists of a magnetic fastening device, such as used on purses or similar, there is no need for an additional permanent magnet. Instead the bias-field from the magnetic fastening system may be used in the system according to the invention. The permanent magnet as shown is rectangular in shape but may in other embodiments be in the form of small metallic pieces of various shapes and sizes (such as those used domestically as kitchen pin-up devices on the refrigerator), powder, granules, film, magnetic ink, and other existing forms.

The thickness of the magnet may also range between about 30 µm-5 mm, such as about 40 µm-3 mm. 70 µm-2 mm, 100 µm-2 mm, 500 µm-2 mm. 1 mm-2 mm. 30 µm-1 mm. 30 µm-500 µm, or 30 µm-200 µm.

A "thin" magnet may have a thickness of about 40 µm, while a typical "thick" magnet may have a thickness of about 1 mm. The length and width of the magnet is preferably adapted for each use. Typically the magnet has at least one dimension, such as a length, width, diameter or similar, of at least 5 mm, 10 mm, 2-10 mm, 20 mm, 30 mm, 40 mm, 50 mm or about 10-20 mm, such as 10-30 mm, 10-40 mm, 10-50 mm, 10-100 mm. Different magnets gives different bias-fields which affect the resonance of the magnetoelastic film. A plurality of permanent magnets may be used in one embodiment.

Example 4

An excitation device is used to excite the resonant entity of the embodiments of the present invention. Said excitation device comprises in one embodiment an excitation coil, and suitable circuitry and power supply to provide said coil with a signal suitable for generating a radio frequency excitation field.

A reading device is used to pick up the response signal emitted from the resonant entity. Said reading device comprises in one embodiment a pickup coil, and suitable circuitry and power supply to receive and extract frequency data from said response signal. Said reading device further comprises a display for displaying said frequency. In a further embodiment said reading device further comprises circuitry or software to determine whether a frequency refers to a correctly fastened absorbent article or to a an unfastened/removed absorbent article.

Example 5

In a further embodiment of the present invention said absorbent article is provided with a seal means. Said seal means comprises a first part and a second part.

Said first part is provided with an influencing means. Said second part is provided with a resonant entity, capable of being influenced by said influencing means.

Said first part and said second part are devised to be able to attach to each other, i.e. the seal is closed, such that when they are attached the influencing means is influencing the resonant entity. When taken apart from each other, i.e. the seal is broken, the influencing means do not influence said resonant entity to any significant degree.

The seal means is arranged at the absorbent article in such a way that, when the absorbent article is properly attached to the user, and the seal means is closed, it is not possible to remove or displace the absorbent article without breaking the seal.

When the seal is broken the response from the resonant entity is altered and the event can be detected.

Preferably, the influencing means is provided within or upon an adhesive tape, and when the absorbent article, e.g. a trouser type diaper, is properly put into place, the adhesive tape is attached to the part comprising the resonant entity, thereby influencing the resonant entity.

When the trouser type diaper is removed or displaced, intentionally or unintentionally, the tape will be displaced from its position, and the influence on the resonant entity is altered. The response from said entity is thus altered and the event can be detected.

The invention should not be considered as limited by the above description; rather the scope and limitations of the invention are defined by the enclosed claims, and equivalents thereof.

What is claims is:

1. A system comprising means for detecting when an absorbent article is unfastened or removed from a body of a wearer, by detecting displacement of one part of the absorbent article from a position in contact with another part of the absorbent article to a position not in contact with the another part of the absorbent article, and means for conveying an alarm signal if the absorbent article is unfastened or removed from the body of the wearer, wherein the absorbent article comprises at least one absorbent layer and an object to be displaced, and the means for detecting includes a remote receiver that is remote from the absorbent article.

2. The system according to claim 1, wherein said means for detecting detects oscillational differences arising due to an increase or a decrease in a magnetic bias-field corresponding to a displacement of said object.

3. The system according to claim 2, wherein said means for detecting is a magnetoelastic film.

4. The system according to claim 1, wherein said means for detecting comprises a radiofrequency electrical circuit.

5. The system according to claim 4, wherein said radiofrequency electrical circuit is arranged such that it becomes short-circuited when said absorbent article is fastened correctly to the body of the wearer.

6. The system according to claim 5, wherein said radiofrequency electrical circuit is arranged such that it is not short-circuited when said absorbent article is unfastened or removed from the body of the wearer.

7. The system according to claim 6, further comprising an excitation device capable of emitting a radio frequency excitation signal.

8. The system according to claim 7, wherein said remote receiver is capable of reading a radio frequency signal emitted from the radiofrequency electrical circuit.

9. The system according to claim 1, wherein said remote receiver is a handheld unit.

10. The system according to claim 1, wherein said remote receiver is a stationary unit.

11. The system according to claim 1, further comprising means for detecting when said article is wet, and also comprising means, connected to said means for detecting when said article is wet, for conveying an alarm signal, signalling that said article is wet.

12. A system comprising a sensor for detecting when an absorbent article is unfastened or removed from a body of a wearer, by detecting displacement of one part of the absorbent article from a position in contact with another part of the absorbent article to a position not in contact with the another part of the absorbent article, and an alarm for conveying an alarm signal if the absorbent article is unfastened or removed from the body of the wearer, wherein the absorbent article comprises at least one absorbent layer and an object to be displaced, and the sensor includes a remote receiver that is remote from the absorbent article.

13. The system according to claim 12, wherein said sensor detects oscillational differences arising due to an increase or a decrease in a magnetic bias-field corresponding to a displacement of said object.

14. The system according to claim 13, wherein said sensor includes a magnetoelastic film.

15. The system according to claim 12, wherein said sensor includes a radiofrequency electrical circuit.

16. The system according to claim 15, wherein said radiofrequency electrical circuit is arranged such that it becomes short-circuited when said absorbent article is fastened correctly to the body of the wearer.

17. The system according to claim 16, wherein said radiofrequency electrical circuit is arranged such that it is not short-circuited when said absorbent article is unfastened or removed from the body of the wearer.

18. The system according to claim 17, further comprising an excitation device capable of emitting a radio frequency excitation signal.

19. The system according to claim 18, wherein said remote receiver is capable of reading a radio frequency signal emitted from the radiofrequency electrical circuit.

20. The system according to claim 12, wherein said remote receiver is a handheld unit.

21. The system according to claim 12, wherein said remote receiver is a stationary unit.

22. The system according to claim 12, further comprising means for detecting when said article is wet, and also comprising means, connected to said means for detecting when said article is wet, for conveying an alarm signal, signalling that said article is wet.

23. A system comprising:
  an absorbent article including a liquid permeable topsheet, a liquid impermeable bottom sheet, and an absorbent core between the liquid permeable topsheet and the liquid impermeable bottom sheet,
  means for detecting when the absorbent article is unfastened, and
  means for conveying an alarm signal if the absorbent article is unfastened.

24. The system according to claim 1, wherein the means for detecting includes a resonant entity.

25. The system according to claim 12, wherein the sensor includes a resonant entity.

* * * * *